United States Patent [19]

Kelly et al.

[11] Patent Number: 5,624,670
[45] Date of Patent: Apr. 29, 1997

[54] USE OF INTERLEUKIN-8 FOR INDUCING CERVICAL RIPENING

[75] Inventors: Rodney W. Kelly, Edinburgh, Great Britain; Kristof Chwalisz, Berlin, Germany; Radostaw Bukowski, Berlin, Germany; Peter Scholz, Berlin, Germany

[73] Assignee: Medical Research Council, United Kingdom

[21] Appl. No.: 244,274

[22] PCT Filed: Nov. 23, 1992

[86] PCT No.: PCT/EP92/02690

§ 371 Date: Feb. 23, 1995

§ 102(e) Date: Feb. 23, 1995

[87] PCT Pub. No.: WO93/09796

PCT Pub. Date: May 27, 1993

[30] Foreign Application Priority Data

Nov. 21, 1991 [GB] United Kingdom ............... 9124775

[51] Int. Cl.⁶ .................................................. A61K 38/20
[52] U.S. Cl. ............................................. 424/85.2; 514/12
[58] Field of Search ................................ 424/85.2, 85.1; 514/2, 12, 21; 530/357

[56] References Cited

U.S. PATENT DOCUMENTS 4,870,067  9/1989  Chwalisz et al. ................ 514/171

FOREIGN PATENT DOCUMENTS

| 0214924 | 7/1986 | European Pat. Off. |
| WO89/04836 | 6/1989 | WIPO |
| WO91/08483 | 6/1991 | WIPO |

OTHER PUBLICATIONS

Kelly et al, "Choriodecidual Production of Interleukin-8 and Mechanism of Parturition", The Lancet, vol. 339, No. 8796, 28 Mar. 1992, London, GB.

Romero et al, "Neutrophil Attractant/Activating Peptide–1/Interleukin–8 in Term and Preterm Parturition", American Journal of Obstetrics and Gynecology, vol. 165, No. 4, Oct. 1991, pp. 813–820.

Colditz, "Effect of Exogenous Prostaglandin E2 and Actinomycin D on Plasma Leakage Induced by Neutrophil–Activating Peptide–1/Interleukin–8", Immunology and Cell Biology, vol. 68, Dec. 1990, pp. 397–403.

Ulmsten Ulf et al, "A New Gel For Intracervical Application of Prostaglandin E2", Chemical Abstracts, vol. 92, No. 7, 18 Feb. 1980, Columbus, Ohio, US.

Prostaglandins Jul. 1987 vol. 34 No. 1 pp. 119–Rath et al "The Role of Collagenases and Proteases in Prostaglandin–induced Cervical Ripening".

Contraception Mar. 1990 vol. 41 No. 3 p. 283 Rødestad et al "Induced Cervical Ripening . . . ".

Cytokine vol. 3 No. 1 Jan. 1991 p 21–27 Rot "Chemotactic Potency of Recombinant . . . ".

*Primary Examiner*—Ponnathapura Achutamurthy
*Attorney, Agent, or Firm*—Nixon & Vanderhye

[57] ABSTRACT

The invention provides the use of interleukin-8 or functional derivative thereof for manufacture of a medicament for inducing cervical ripening in a female mammal. The invention provides the use of the compounds of the invention in connection with birth or abortion. Further the invention provides the use of the compounds of the invention in connection with surgical procedure and diagnostic procedure.

22 Claims, 2 Drawing Sheets

USE OF INTERLEUKIN-8 FOR INDUCING CERVICAL RIPENING

BACKGROUND OF THE INVENTION

1. Field of the Invention:

This invention relates to a treatment for ripening of the cervix, particularly in the induction of labour to assist mammals to give birth or in connection with surgical or diagnostic procedure.

2. Description of the Related Art:

Parturition (expulsion of the fetus from the uterus), requires both contractions of the myometrium, the smooth muscle of the uterus, and a softening of the connective tissue of the cervix, so that it will stretch and dilate sufficiently to allow the fetus to be expelled. This softening is known as "ripening".

The current preferred method of cervical ripening is by the use of prostaglandin $E_2$. This is used as a vaginal gel or tablet or as a gel placed in the cervix. One worry about the use of prostaglandin $E_2$ is that there is a possibility of hyperstimulation of the uterus, leading to excessively strong myometrial contractions before the cervix is ripened and therefore before a comfortable or safe birth is possible. The ideal preparation would soften and efface the cervix without causing myometrial contractions. This would allow the subsequent contractions (induceable if necessary with a small dose of prostaglandin) to deliver the baby with a minimum of resistance. There is good evidence from animal experiments that the antiprogestins such as RU486 would meet these requirements, but the problem with this drug is that is has associated antiglucocorticoid activity which might be detrimental to the fetus.

SUMMARY OF THE INVENTION

It has now surprisingly been found that the final common pathway in prostaglandin and antiprogestin action is the release of interleukin-8. It follows that this compound could be used to induce labour and ripen the cervix. Its use would be without the myometrial contractility associated with the use of prostaglandin and would not prejudice the fetus. During birth the cervix normally ripens without help from outside. But the compound of the invention will help during the normal ripening and during all birth situation in which the ripening is not sufficient. Further the compound of the invention will support the normal ripening to make that process of the birth easier for women.

The advantage of the use of interleukin-8 is the reduction or the avoiding pain during birth, abortion, surgical and diagnostic treatment.

The amino acid sequence of natural interleukin-8 differs from species to species. The proteins differs so much that the interleukin-8 from one species might not work in another species. A test will show in each case whether the protein of one species is compatible with use in another species. Therefore, the effective amount of the protein of the invention will depend upon the origin of the protein and the species to which the protein is administered.

The invention provides the use of (aa) interleukin-8 or (bb) a functional derivative thereof for manufacture of a medicament for inducing cervical ripening in a female mammal. Female mammal can be human being or an aminal, preferred human beings. Further the invention comprises a method for inducing cervical ripening in female human or animal in a need of such inducing comprising administering to said animal a safe and effective amount of (aa) interleukin-8 or (bb) a functional derivative thereof for said ripening.

The invention provides the use of the compounds of the invention in connection with birth or abortion. In this situation of pregnancy the cervix is pre-treated. The hormones during pregnancy alter the cervix which is then inclined to respond effectively to other stimulants. Further the invention provides the use of the compounds of the invention in connection with surgical procedure and diagnostic procedure. Therefore, the compounds of the invention can be used for the following indications:

(A) induction of labour at term (time of ordinary birth, can be combined with sequential treatment with oxytocin or similar agents), (B) induction of labour in connection with a pathological pregnancy (e.g. fetal malformation); (preferred second trimester abortion), (C) induction of labour in connection with intrauterine fetal death, (D) induction of abortion (preferred second trimester abortion), (E) induction of preterm labour, (F) induction of cervical ripening of a non-pregnant female or pregnant female to assist for surgical or diagnostic procedure, and (G) induction of cervical ripening for female to be treated by in vitro fertilisation. In principle the compound can be used for human and non-human females. Human beings are the preferred group for this treatment.

Further the invention comprises the use of (aa) interleukin-8 or (bb) a functional derivative thereof for manufacture of a medicament for inducing cervical ripening in a female mammal, wherein the (aa) interleukin-8 or (bb) functional derivative thereof is co-administered with prostaglandin $E_2$. Additionally the invention comprises a method for inducing cervical ripening in female human or animal in a need of such inducing comprising administering to said human or animal a safe and effective amount of (aa) interleukin-8 or (bb) functional derivative thereof for human or animals wherein the (aa) interleukin-8 or (bb) functional derivative thereof is co-administered with prostaglandin $E_2$. The co-administration is used in connection with birth or abortion.

Further the invention comprises the use of (aa) interleukin-8 or (bb) functional derivative thereof for manufacture of a medicament for inducing cervical ripening in a female mammal, wherein the (aa) interleukin-8 or (bb) functional derivative thereof is co-administered with an uterotonic effective compound. Additionally the invention comprises a method for inducing cervical ripening in female human or animal in a need of such inducing comprising administering a safe and effective amount of (aa) interleukin-8 or (bb) functional derivative thereof for human or animals, wherein the (aa) interleukin-8 or (bb) functional derivative thereof is co-administered with an uterotonic effective compound. The co-administration is used in connection with birth or abortion.

Uterotonic effective compounds are described in the European publications No.: EP 0 21 4 924 (filed 25 Jul. 1986) and No.: EP 0 184 471 (filed 22 Feb. 1985) which both are incorporated by reference.

The preferred uterotonic effective compound is oxytocin. The doses and the form of application are also mentioned in the European patent specification No.: 0 214 924 B1 which has been granted on 26 Aug. 1992.

Further the invention provides a combination of (i) prostaglandin $E_2$ and (ii) (aa) interleukin-8 or (bb) functional derivative thereof for manufacture of a medicament for cervical ripening in a female mammal in connection with birth or abortion.

In a further embodiment the invention comprises a product containing (i) prostaglandin $E_2$ and (ii) (aa) interleukin-8 or (bb) functional derivative thereof as a combined preparation for simultaneous, separate or sequential use in connection with birth or abortion of female mammal.

Further the invention comprises a product containing (i) an uterotonic effective compound and (ii) (aa) interleukin-8 or (bb) functional derivative thereof as a combined preparation for simultaneous, separate or sequential use in connection with birth of abortion of female mammal.

Also the both compounds can be administered by different pathways (for example gel and injection) and at different times (for example first interleukin-8 after 6 to 48 hours oxytoxin), the two compounds form a unit, they belong to the same indication. They can be used as a kit. The effect of one compound is supported by the effect of the other compound.

The invention accordingly provides the use of interleukin-8 or a functional derivative thereof in inducing cervical ripening and a method of assisting mammalian birth or fetal removal, which comprises administering to the cervix of a pregnant mammal an amount of interleukin-8 or a functional derivative thereof effective to induce cervical ripening.

The invention also includes a gel or cream comprising interleukin-8 or a functional derivative thereof and a gel-forming or cream-forming vehicle.

In another aspect the invention includes a composition for application to the cervix which comprises (1) interleukin-8 or a functional derivative thereof, (2) a substance which induces myometrial contractions and (3) a pharmaceutically acceptable carrier or diluent.

DESCRIPTION OF THE PREFERRED EMBODIMENTS

Figure 1A:
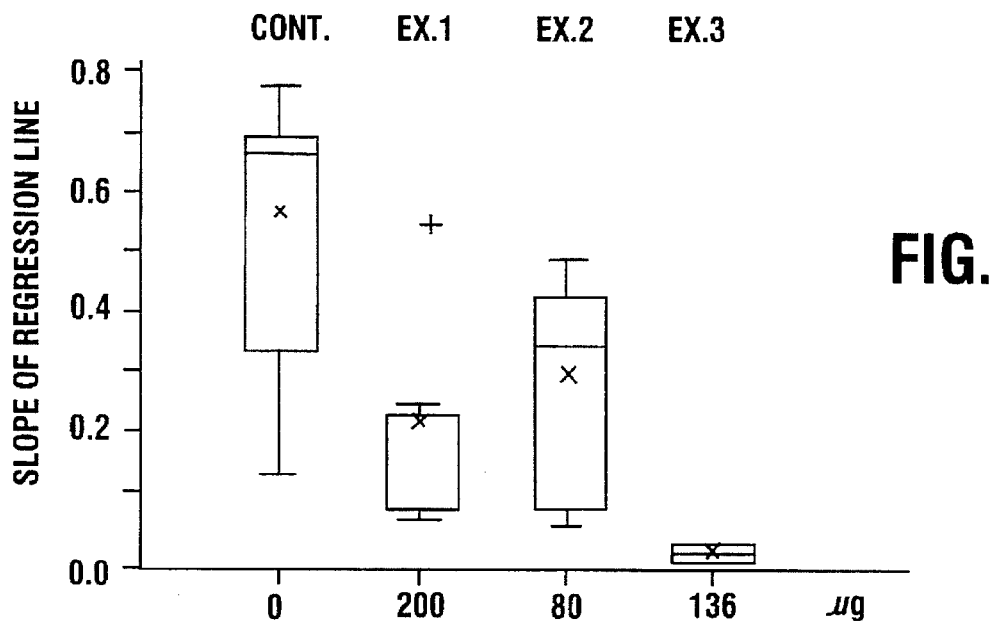
FIG. 1 shows the effect of interleukin-8 on cervical ripening in pregnant guinea pigs.

Interleukin-8 is also known as neutrophil activating peptide-1 and previously known as neutrophil activation factor (A. WALZ et al., Biochem Biophys Res Commun 149, 755–761 (1987)), monocyte-derived neutrophil activating peptide (J. M. Schroder et al., J Immuno 1139, 3474–3483 (1987)), or monocyte-derived neutrophil chemotactic factor (T. Yoshimura et al., J Immunol 139, 788–793 (1987) and Proc Natl Acad Sci USA 84, 9233–9237 (1987)). Interleukin-8 can be obtained from cellular sources, as described above and by M. Baggiolini et al., J Clin Invest 84, 1045–1049 (1989), or by culturing chorio-decidual cells stimulated by protein kinase C or by phorbol myristyl acetate (PMA). More conveniently, it is obtainable by recombinant DNA synthesis, see J. Lindley et al., Proc Nat Acad Sci USA 85, 9199–9203 (1988) or by peptide synthesis, see I. Clark-Lewis et al., Biochemistry 30, 3128–3135 (1991).

Human interleukin-8 exists in various forms which differ at the N-terminal end. The mature protein is generally reckoned to be 72 amino acids long beginning with a serine residue. This is the currently preferred form of interleukin-8 for use in this invention.

The term "functional derivatives" is intended to include the "fragments", "variants", "analogues", "chemical derivatives" or "polymeric forms" of interleukin-8. A "fragment" of interleukin-8 refers to polypeptide subsets. A "variant" refers to a naturally occurring molecule substantially similar to either the entire molecule or a fragment thereof. An example is the 77 amino acid long, alanine-terminated polypeptide described in PCT Patent Application Publication No. WO 91/08231 (Bringham and Woman's Hospital). An "analogue" of interleukin-8 is meant to refer to a non-natural molecule substantially similar to either the entire molecule or a fragment thereof. A molecule is said to be "substantially similar" to another molecule if the sequence of amino acids in both molecules is substantially the same, and if both molecules possess a similar biological activity. Thus, provided that two molecules possess a similar activity, they are considered variants, as that term is used herein, even if one of the molecules contains additional amino acid residues not found in the other, or if the sequence of amino acid residues is not identical.

A "chemical derivative" of interleukin-8 contains additional chemical groups not normally a part of the molecule. Such chemical groups may improve the molecule's solubility, absorption, biological half-life, etc. They may alternatively decrease the toxicity of the molecule or eliminate or attenuate any undesirable side effect of the molecule. Examples of chemical groups giving rise to such effects are disclosed in Remington's Pharmaceutical Sciences (1980) and will be apparent to those of ordinary skill in the art. Polymeric forms of interleukin-8 are those having repeated units of the monomeric form. Such forms appear to exist in solution.

The interleukin-8 or functional derivative can be administered in any way in which, directly or indirectly, it will reach the cervix. Thus, it is conveniently applied intravaginally or directly to the cervix, e.g. typically as a gel or cream. It can also be injected into the cervical tissue or by a blunt needle into the cervical channel. It can also be applied extra-amniotically, i.e. between the uterine wall and the amniotic sac, using a catheter.

The preferred formulation is a gel or cream, but it can be applied as softenable capsules, liposomes or in a slow release formulation, or as an aqueous solution, e.g. a saline or protein-containing solution.

The compound or the invention exhibit pharmacological activity in induction of cervical ripening and may, therefore, be useful as a pharmaceutical agent. The measurement of the cervix ripening is described in Example 1. Interleukin-8 consisting of 72 amino acids beginning with serine (published in I. Clark-Lewis et al. (1991) Biochemistry 30:3128–3135) shows an effect on the cervical ripening at dosages of from about 0.001 to about 0.2 mg when administered to pregnant female guinea-pigs. For these indications mentioned before under (A) to (E) the appropriate dosage will, of course, vary depending upon, for example, the compounds of the invention employed, the host, the mode of administration and the nature and severity of the condition being treated. However, in general, satisfactory results in animals are indicated to be obtained at a dosage from about 0.01 to about 2 mg per cervix, preferred at a dosage of from about 0.05 to 0.4, most preferred 0.1 to 0.2 mg per cervix. The compound of the invention can be administered 6 to 48 hours before the final ripening of the cervix. The ripening can be proceeded by induction of labour with a oxytocin compound. The compound can be administered in one or more dosages administered in a series with a distance of some hours or one day. The compound of the invention may be administered by any conventional route, in particular in form of gel, ointment or local injection.

Interleukin-8 consisting of 72 amino acids beginning with serine shows an effect on the cervical ripening at dosages of from about 0.01 to about 20 mg when administered to female guinea-pigs which are not pregnant. For these indications mentioned before under (F) to (G) the appropriate dosage will, of course, vary depending upon, for example, the compounds of the invention employed, the host, the mode of administration and the nature and severity of the condition being treated. However, in general, satisfactory results in animals are indicated to be obtained at a dosage from about 0.1 to about 20 mg per cervix, preferred at a dosage of from about 0.5 to 4, most preferred 1 to 2 mg per cervix. The compound of the invention can be administered 24 or 48 hours before the final ripening of the cervix. The compound can be administered in one or more dosages administered in a series with a distance of some hours or one day. The compound of the invention may be administered by any conventional route, in particular in form of gel, ointment or local injection.

The present invention provides pharmaceutical compositions comprising compounds of the invention in association with at least one pharmaceutical carrier or diluent which composition is used for the above mentioned utility. Such compositions may be manufactured in a conventional manner. In human therapy unit dosage forms contain, for example, from about 0.1 to 200 mg of the compounds of the invention when administered to pregnant women. When administered to non-pregnant women the unit dosage forms contain, for example, from about 0.1 to 200 mg of the compounds of the invention.

Further the invention comprises a product containing (i) prostaglandin $E_2$ and (a) interleukin-8 or (b) functional derivative thereof and (ii) prostaglandin $E_2$ and/or an uterotonic effective compound as a combined preparation for a simultaneous use of (i) prostaglandin $E_2$ and (a) interleukin-8 or (b) functional derivative thereof and a sequential use of the compounds of (i) and (ii) in connection with birth or abortion of female mammal wherein the compounds under (i) are administered before the compounds under (ii).

Preferably the compounds which are given simultaneously are co-administered in a gel. But a separate administration is possible. The first combination is given 6 to 48 before the compounds under (ii).

The combination of a prostaglandin or uterotonic compound and interleukin-8 comprises first an administration of interleukin-8 and later the administration of the prostaglandin or uterotonic compound. The time between the administration of the fist and the second compound lasts from about 6 to about 48 hours.

The dosages of the prostaglandin or uterotonic compound will be according to the dosages mentioned in the state of art.

The amount of interleukin-8 applied might be in the range 0.01 to 20 mg.

The time of the application will depend on the course of the labour, since in birth it is desirable to ensure that the cervix is ripened before the myometrial contractions have begun or are about to begin. Administration can be all at once, in divided doses or by slow release.

As well as its use in assisting labour, whether in a natural or surgically assisted procedure, interleukin-8 or a functional derivative is useful in removing an unwanted fetus, e.g. in an abortion procedure, which may also be natural or surgically assisted.

The invention includes certain composition per se, notably gel or cream formulations comprising interleukin-8 or a functional derivative thereof and a gel-forming or cream-forming vehicle, respectively. It is believed that these are novel. The gels and creams may contain suitable aqueous or oleagious substances as the vehicle, as is well known in the art.

Also believed novel are any pharmaceutical composition which comprises (i) interleukin-8 or a functional derivative thereof, (ii) a prostaglandin and most especially $PGE_2$ and (iii) a pharmaceutically acceptable diluent or carrier. Such a composition is included as part of the invention in any of the forms referred to above or below. $PGE_2$ and interleukin-8 act synergistically. Therefore, the combination of those two compounds results in the increase in efficacy and dose reduction.

More generally, with respect to the novel use of interleukin-8 or a functional derivative thereof, this active ingredient can be formulated as a gel or cream, especially a syringeable gel, or as capsules, suppositories, or slow or delayed release formulations. Gels will usually be of hydrophilic polymers such as cross-linked polyethylene glycol, cross-linked starch or polyvinyl pyrrolidone. Capsules can be made of a polymer which is softenable by body heat, such as gelatine or a polymer which slowly dissolves in body fluids. Many slow release compositions are well known, e.g. of the matrix type (see, for instance, U.S. Pat. No. 3,851, 648) or a membrane device.

The invention applies to humans and to any other mammal which has a fundamental parturition mechanism similar to that of humans, in that cervical ripening is required.

Figure 1B:
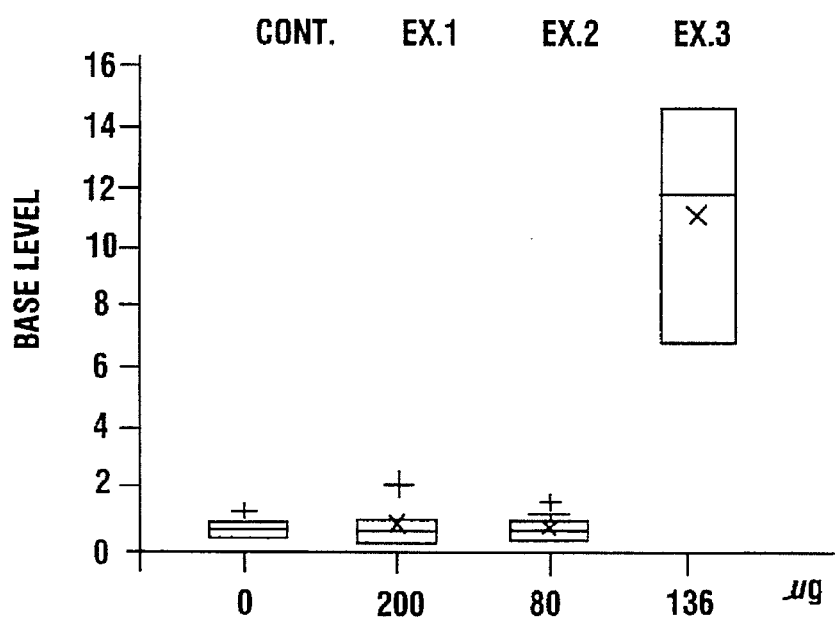

The results of the invention are supported by the Figures which show the following:

FIG. 1 shows the effect of interleukin-8 on cervical ripening in pregnant guinea pigs. Animals of Examples 1 and 2 are treated with 200 µg/d interleukin-8 twice and with 80 µg interleukin-8 on day 49 post coitum. Animals of Example 3 are treated with 136 µg interleukin-8 on days 59 and 60. The upper panel demonstrates the effect on the extensibility (slope of the regression curve), the lower panel shows the initial dilatation (in mm) during extensibility measurement. The data are presented as box plots. The vertical lines represent the range from the lowest to the highest amount. The height of the box, the horizontal line, and asterisk describe the inter quartile range, median, and mean value, respectively.

and

Figure 2A:
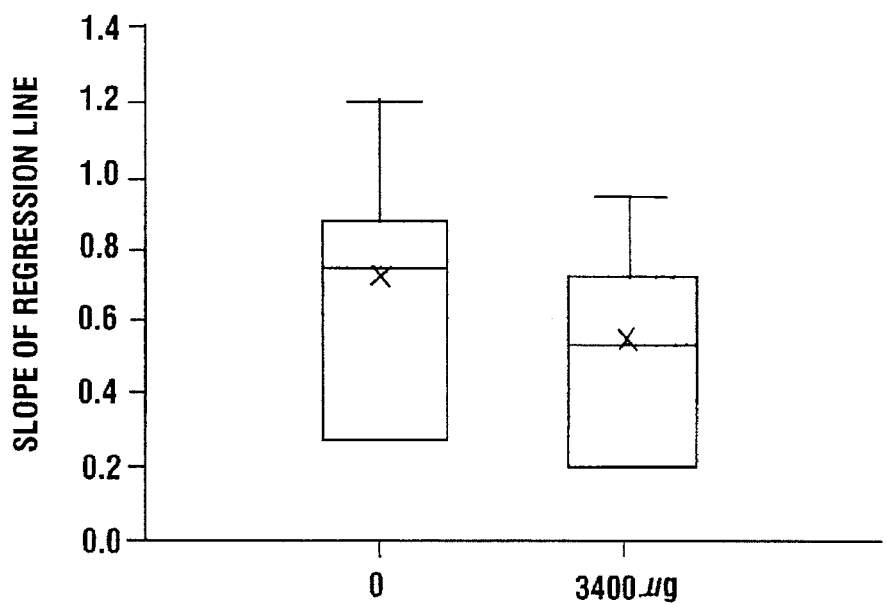
FIG. 2 shows the effect of interleukin-8 on non-pregnant guinea pigs.
Figure 2B:
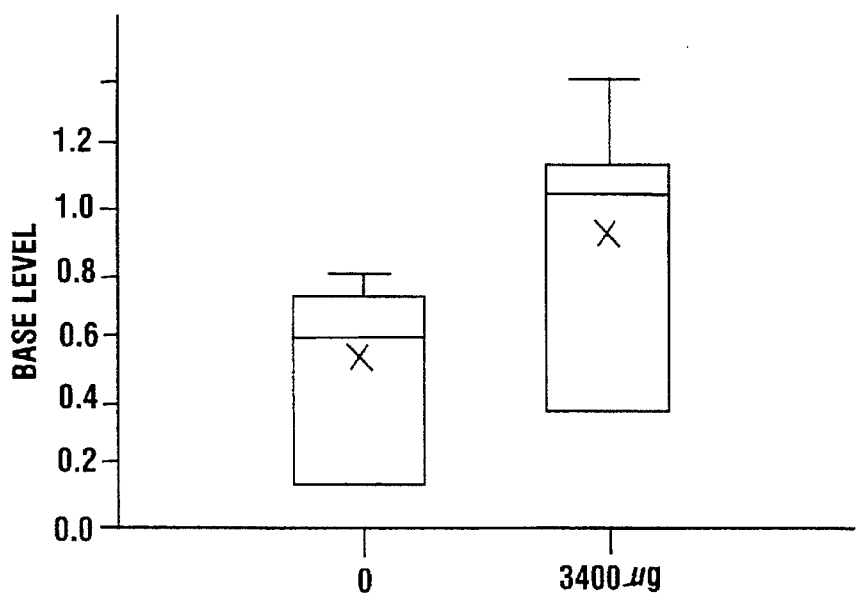

FIG. 2 shows the effect of interleukin-8 on cervical ripening in non-pregnant guinea pigs. The upper panel demonstrates the effect on the extensibility (slope of the regression curve). The lower panel shows the initial dilatation (in mm) during extensibility measurement. Data are presented as box-plots as described for FIG. 1.

EXAMPLES

EXAMPLE 1

The influence of interleukin-8 on cervical ripening in pregnant guinea pigs using two doses (a) General Part:

Measurement of the ripening:

Entire cervices are obtained from guinea pigs at day 50 post coitum. The extensibility studies are performed by a modification of the method described in the publication DOWNING, S. J. and SHERWOOD, O. D. (1985) Endocrinology 116: 1215–1220.

The isolated cervix is mounted between two hooks inserted through each canal of the cervix. One hook is fixed, the other is moved upwards while force and displacement are measured with a sampling rate of 1 Hz.. First each cervix is extended until a force of 50 mN is reached. The associated displacement is recorded and will be called initial dilation. Thus the original inner circumference of the cervix is double the initial dilation.

Afterwards the cervix is extended by moving the hook for 0.1 mm, then the hook is fixed and the cervix allowed to relax for 2 minutes. This is repeated until either the cervix ruptures or at least the yield point has been reached, i.e. the envelope of the load vs. time curve becomes non-linear (see the publication CONRAD, J. T. and UELAND, K. (1979) Am J Obstet Gynecol 133:11–13)

(b) Analysis:

To determine the extensibility of the cervix the force vs. stretch ratio curve is studied. This curve is obtained by taking the maximum force at each extension stage and the associated stretch ratio, which is defined as displacement divided by the initial dilation. The slope of a regression line through the linear portion of this curve is taken to quantify the effect of treatment on cervical extensibility. A decrease in the slope represents an increase in the cervical extensibility (ripening effect).

(c) Special part:

Pregnant guinea pigs which are at day 48 and 49 post coitum (n=6 animals per group) are treated with 200 µg interleukin-8 in gel intracervically on day 48 and additionally with 200 µg human interleukin-8 in gel intracervically on day 49. The autopsy is made on day 50.

The gel is administered by the following method: After introduction of the speculum into vagina, 200 µl of cellulose gel with or without compound is injected through ca 100 mm long blunt needle into cervical channel. Part of the gel moves along the channel to take place around os internum of the uterine cervix. The Gel has the following formulation: The gel comprises the compounds of the invention in PBS (phosphate buffered saline, see L. HUDSON and F. C. HAY (1980) Practical Immunology, Oxford, sec. edition) with 3% (w/v) hydroxylethylcellulose.

The interleukin-8 is recombinant human interleukin-8 and has the sequence of comprising 72 amino acids starting with serine.

The control group receives a gel comprising 3% (w/v) hydroxylethylcellulose in PBS.

The mechanical properties of the cervix are measured by the method described above which allows the quantification of cervical extensibility and dilation of the uterine cervix under isometric conditions.

(d) Results:

The results of the Examples 1 to 3 are shown in FIG. 1. The upper panel shows the slopes of the regression line which is the parameter of the extensibility of the cervix. The lower panel demonstrates the initial dilatation in mm of the cervix.

The results demonstrate a dose-dependent ripening effect of interleukin-8 after local administration in gel (see Examples 1 and 2). The test in Example 3 demonstrates that interleukin-8 does not induce labour after intrauterine administration. Example 3 shows a dramatic ripening effect on the cervix.

EXAMPLE 2

The influence of interleukin-8 on cervical ripening in pregnant guinea pigs using one dose The animals are treated as described in Example 1. Instead of giving two doses of 200 µg per dose of interleukin-8 the animals get one dose of 80 µg interleukin-8 on day 49 post coitum. To save animals the control group of Example 1 is taken. The results are shown in FIG. 1 and discussed in Example 1d.

EXAMPLE 3

The influence of interleukin-8 on cervical ripening in pregnant guinea pigs using two doses and tested on day 63 post coitum In contrast to Example 1 the animals are treated for two days (on 59 and 60 post coitum) with 136 µg human interleukin-8 per day. The compound is injected transcervically, extraamniotically into the uterine cavity in 200 µl PBS-buffer as mentioned above. Since the animals do not deliver till day 63 post coitum the autopsy is performed on day 63 post coitum. The results are shown in FIG. 1 and discussed in Example 1d.

EXAMPLE 4

The influence of interleukin-8 on cervical ripening in non-pregnant guinea pigs using one dose a) Test Conditions:

The animals which are non-pregnant are treated according to Example 1 with the following exceptions. Four animals are given 3,400 µg human interleukin-8 in 200 µl gel. The gel is intracervically administered. The control animal are treated with only gel, the autopsy and the extensibility measurements are practised 18 hours after gel application.

b) Results:

The results are shown in FIG. 2. The local application of interleukin-8 increase the dilatation of the cervix (lower panel) and slightly lowers the slope of the extensibility curve

EXAMPLE 5

Interleukin-8 (0.5 mg) in aqueous solution is added to 0.1 g of cross-linked starch and the polymer is allowed to absorb the solution. The preparation is the freeze-dried and stored dry. Before application by the physician, physiological saline is added to the polymer to give a gel of the required consistency for application by syringe. The gel is then introduced into the cervix using a syringe and blunt needle.

We claim:

1. A method of inducing cervical ripening in a female mammal in need of such inducing, which method comprises the step of administering to the said mammal a safe and effective amount of an interleukin-8 or a functional derivative thereof.

2. A method according to claim 1 wherein the said mammal is a woman.

3. A method according to claim 1 wherein the said mammal is pregnant.

4. A method according to claim 3 wherein the said interleukin-8 or functional derivative thereof is administered to induce cervical ripening in connection with labour.

5. A method according to claim 3 wherein the said interleukin-8 or functional derivative thereof is administered to induce cervical ripening in connection with abortion.

6. A method according to claim 3 wherein prostaglandin $E_2$ is co-administered.

7. A method according to claim 3 wherein oxytocin is co-administered.

8. A method according to claim 3 wherein prostaglandin $E_2$ or oxytocin is administered from about 6 hours to about 48 hours after the administration of the said interleukin-8 or functional derivative thereof.

9. A method according to claim 1 wherein the said interleukin-8 or functional derivative thereof is human interleukin-8 or a functional derivative thereof.

10. A method according to claim 1 wherein from 0.01 to 20 mg of said interleukin-8 or functional derivative thereof is administered.

11. A method according to claim 1 wherein the interleukin-8 or functional derivative thereof is applied intravaginally or directly to the cervix as a gel or cream or is injected into the cervical tissue or into the cervical channel.

12. A method of inducing cervical ripening in a pregnant woman in need of such inducing, which method comprises the step of administering to the cervix of the said woman from about 0.01 to 200 mg of human interleukin-8.

13. A method according to claim 12 wherein the said interleukin-8 is administered to induce cervical ripening in connection with labour.

14. A method according to claim 12 wherein the said interleukin-8 is administered to induce cervical ripening in connection with abortion.

15. A method according to claim 12 wherein prostaglandin $E_2$ or oxytocin is administered from about 6 hours to about 48 hours after administration of the said interleukin-8.

16. A method according to claim 12 wherein interleukin-8 is applied intravaginally or directly to the cervix as a gel or cream or is injected into the cervical tissue or into the cervical channel.

17. A method of assisting birth or fetal removal, which method comprises the step of administering to the cervix of a pregnant woman an amount of human interleukin-8 or a functional derivative thereof effective to induce cervical ripening.

18. A method according to claim 17 wherein prostaglandin $E_2$ or oxytocin is administered from about 6 hours to about 48 hours after administration of the said interleukin-8 or functional derivative thereof.

19. A method according to claim 17 wherein from 0.01 to 20 mg of said interleukin-8 or functional derivative thereof is administered.

20. A method according to claim 17 wherein interleukin-8 or functional derivative thereof is applied intravaginally or directly to the cervix as a gel or cream or is injected into the cervical tissue or into the cervical channel.

21. A method according to claim 1 wherein from 0.001 to 20 mg of said interleukin-8 or functional derivative thereof is administered.

22. A method according to claim 17 wherein from 0.001 to 20 mg of said interleukin-8 or functional derivative thereof is administered.

* * * * *